United States Patent [19]

Beeny et al.

[11] 4,272,278

[45] Jun. 9, 1981

[54] 1-METHYL-2-ARYL-2,3-DIHYDRO-1H-2,1-BENZAZAPHOSPHOLE-1-OXIDES, HERBICIDAL COMPOSITIONS AND THE USE THEREOF

[75] Inventors: Mark T. Beeny, Maryland Heights; James A. Miles, Olivette, both of Mo.

[73] Assignee: Monsanto Company, St. Louis, Mo.

[21] Appl. No.: 148,841

[22] Filed: May 12, 1980

Related U.S. Application Data

[63] Continuation-in-part of Ser. No. 55,432, Jul. 6, 1979, abandoned.

[51] Int. Cl.$^3$ .................... A01N 57/36; C07F 9/65
[52] U.S. Cl. ............................................. 71/86; 564/13
[58] Field of Search ............... 71/86; 564/13; 556/404

[56] References Cited

U.S. PATENT DOCUMENTS

| | | | |
|---|---|---|---|
| 3,449,426 | 6/1969 | Braye | 71/86 X |
| 3,980,618 | 9/1976 | Birum | 260/551 P |
| 4,102,949 | 7/1978 | Schliebs et al. | 260/985 |

OTHER PUBLICATIONS

Collins, et al., Aust. J. Chem., 27, 1759–1765 (1974).
Dennis, et al., J. Am. Chem. Soc., 88, 3431–3432 (1966).
Dannley, et al., J. Org. Chem., 26, 3995–3998 (1961).
Ludt, et al., J. Org. Chem., 36, 1607–1613 (1971).
Hellwinkel, et al., Tetrahedron Letters, No. 37, 3241–3244 (1977).
Eberhard, et al., J. Am. Chem. Soc., 87, 253–260 (1977).
Walborsky, et al., J. Org. Chem., 43, 731–734 (1978).
Miles, et al., J. Org. Chem., 43, 4668–4670 (1978).
Walborsky, et al., Chemical Abstracts, vol. 88, 89736g (4/78).
Lopez, et al., Chemical Abstracts, vol. 75, 49232q (1971).

*Primary Examiner*—Anton H. Sutto
*Assistant Examiner*—Diana G. Rivers
*Attorney, Agent, or Firm*—Patricia A. Coburn; Donald W. Peterson

[57] ABSTRACT

This disclosure relates to novel 1-methyl-2-aryl-2,3-dihydro-1H-2, 1-benzazaphosphole-1-oxides which are useful as herbicides. This disclosure further relates to herbicidal compositions containing such benzazaphospholes and to herbicidal methods employing such compounds and compositions.

15 Claims, No Drawings

1-METHYL-2-ARYL-2,3-DIHYDRO-1H-2,1-BEN-ZAZAPHOSPHOLE-1-OXIDES, HERBICIDAL COMPOSITIONS AND THE USE THEREOF

This application is a continuation-in-part of application Ser. No. 055,432, filed July 6, 1979, now abandoned.

This invention relates to novel 1-methyl-2-aryl-2,3-dihydro-1H-2,1-benzazaphosphole-1-oxides which are useful as herbicides. This invention further relates to herbicidal compositions containing such benzazaphospholes and to herbicidal methods employing such compounds and compositions. The compounds of the present invention are members of a class of bicyclic hetero compounds containing only one phosphorus-nitrogen bond.

The compounds of the present invention are represented by the formula

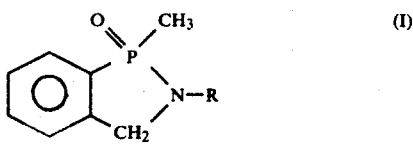

wherein R is selected from the group consisting of phenyl, phenoxyphenyl and substituted phenyl containing from one to three groups individually selected from the class consisting of lower alkyl, lower alkoxy, halogen, and lower haloalkyl. It is preferred that R represents substituted phenyl groups containing 1 or 2 of such substituents.

As employed herein, the terms "lower alkyl" and "lower alkoxy" designate alkyl and alkoxy radicals which have up to 4 carbon atoms in a straight or branched chain. Groups representative of these radicals include, for example, methyl, ethyl, propyl, isopropyl, butyl, isobutyl, sec-butyl, t-butyl, methoxy, ethoxy, propoxy, isopropoxy, butoxy, isobutoxy, sec-butoxy, t-butoxy and the like.

The term "halogen" or "halo" as used herein includes chlorine, bromine, fluorine and iodine.

The term "lower haloalkyl" as employed herein designates alkyl moieties having up to 4 carbon atoms wherein at least one hydrogen atom has been replaced by a halogen atom. Groups representative of these radicals include, for example, chloromethyl, iodobutyl, dichloroethyl, dibromopropyl, trichloromethyl, trifluoromethyl and the like.

Illustrative of the substituted phenyl groups which R represents are mono-substituted phenyl wherein the substitutent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, and the like and the di- and tri-substituted phenyl groups wherein the substituents are the same or different and are located in the 2, 3, 4, 5 or 6 positions of the phenyl ring, for example, dichlorophenyl, difluorophenyl, methylchlorophenyl, butoxyfluorophenyl, methylbutylphenyl, methoxybutoxyphenyl, dimethoxyphenyl, methylphenoxyphenyl, trichlorophenyl, trimethylphenyl, tributoxyphenyl and the like.

In accordance with this invention, the 1-methyl-2-aryl-2,3-dihydro-2,1-benzazaphosphole-1-oxides of formula (I) are prepared by heating a phosphinamide of the formula

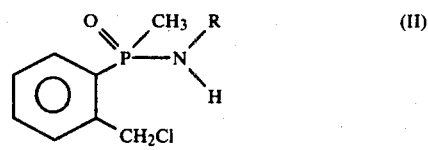

wherein R is above defined; in an aprotic solvent in the presence of a hydrogen halide acceptor within a temperature range of from 20° C. to 200° C.

The temperature at which the process of this invention is conducted is not critical. The temperature should be one which is sufficiently elevated so as to initiate and maintain the reaction. It is preferred to employ temperatures in the range of from 80° C. to 170° C. Generally, the temperature employed is the reflux temperature of the solvent employed.

Due to reactive nature of the various intermediates and reactants, the processes of the present invention should be conducted in an aprotic solvent under essentially anhydrous conditions and in an inert atmosphere. Illustrative of the aprotic solvents employed in the process of this invention include tetrahydrofuran, cyclohexane, methylcyclohexane, hexane, benzene, octane, ethyl ether, dioxane and the like.

In preparing the benzazaphospholes of the present invention, the ratio of reactants is not narrowly critical. For each mole of a phosphinamide of formula (II), one should employ one mole of a hydrogen halide acceptor to obtain a reasonable yield. It is preferred to employ an excess of the hydrogen halide acceptor for ease of reaction and recovery of the reaction products.

Illustrative of the hydrogen halide acceptors employed in the process of this invention include tertiary amines such as triethylamine, pyridine, diisopropylethylamine, 1,5-diazabicyclo[5.4.0]undec-5-ene and the like.

While the processes of this invention can be conducted at atmospheric, sub-atmospheric or super-atmospheric pressure, for convenience and economy it is generally preferred to conduct these processes at atmospheric pressure.

The phosphinamides of formula (II) used as the starting materials in the production of the compounds of this invention are prepared employing the following procedure which, for simplicity, utilizes o-iodotoluene as the starting material.

A mixture of o-iodotoluene and anhydrous nickel chloride is stirred under a nitrogen atmosphere at 160° C. While maintaining the temperature in a range of 160°-170° C., diethylmethylphosphonite is added dropwise to the mixture. Ethyliodide distills rapidly from the mixture. Following the addition of the phosphonite, the reaction mixture is heated at 165°-175° C., for an hour, then cooled. Upon cooling, the reaction mixture is poured onto ice-water and extracted with chloroform. The chloroform extracts are washed with water, dried over magnesium sulfate and then concentrated in vacuo to yield a colorless oil. This oil is treated directly with a solution containing phosphorous pentachloride in benzene and the resulting mixture is refluxed for 1 hour, then concentrated in vacuo to yield an oil. This oil is distilled to yield methyl-o-tolylphosphinyl chloride. The methyl-o-tolylphosphinyl chloride is added to a liter of carbon tetrachloride and the resulting mixture is heated to reflux temperatures by irradiating the mixture using a 275 watt sunlamp mounted below the pyrex glass flask. Chlorine gas is bubbled into the reaction vessel until formation of o-chloromethylphenylmethylphosphinyl chloride is 60-75% complete in order to prevent formation of the dichloro derivative. The irradiation is then stopped and the reaction mixture is concentrated in vacuo to yield an oily residue. The oily residue is fractionally distilled to remove any unreacted methyl-o-tolylphosphinyl chloride to yield o-chloromethylphenylmethylphosphinyl chloride.

The o-chloromethylphenylmethylphosphinyl chloride dissolved in anhydrous ether is added dropwise to a solution containing a primary amine of the formula RNH$_2$ 

wherein R is above defined; in anhydrous ether at 0° C. After stirring for an additional hour, the reaction mixture is filtered and the filter cake is washed with ether and then slurried in 1% aqueous hydrochloric acid at 0° C. The slurry is filtered and the solid residue washed with water and dried over phosphorus pentoxide under high vacuum to yield the phosphinamide starting material of formula (II).

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

Under a static nitrogen atmosphere, a mixture of N-(4-methoxyphenyl)-P-[2-(chloromethyl)phenyl]-P-methylphosphinamide (1.24 g, 0.004 mol) and 1,5-diazabicyclo[5.4.0]undec-5-ene (0.65 g, 0.0041 mol) in 20 ml. of anhydrous tetrahydrofuran was heated at reflux for 4.5 hours and then stirred for 64 hours at 26° C. The reaction mixture was filtered and the filter cake was washed with ethyl acetate. The filtrate was concentrated in vacuo and the resulting residue was dissolved in 30 ml. of methylene chloride. The methylene chloride solution was washed with 1% aqueous hydrochloric acid, 5% aqueous sodium carbonate then water and subsequently dried over sodium sulfate and concentrated in vacuo to yield a beige solid. The beige solid was recrystallized from benzene to yield 1-methyl-2-(4-methoxyphenyl)-2,3-dihydro-1H-2,1-benzazaphosphole-1-oxide as beige crystals. A second crop was obtained from the filtrate to give a total yield of 0.6 g (55% yield) of 1-methyl-2-(4-methoxyphenyl)-2,3-dihydro-1H-2,1-benzazaphosphole-1-oxide having a melting point of 148°-150° C. and the following analysis:

Calculated: C, 65.93; H, 5.90; N, 5.13. Found: C, 65.66; H, 5.98; N, 5.08.

EXAMPLE 2

Under a static nitrogen atmosphere, a mixture of N-(4-bromophenyl)-P-[2-(chloromethyl)phenyl]-P-methylphosphinamide (3.3 g, 0.00925 mol) and 1,5-diazabicyclo[5.4.0]-undec-5-ene (1.5 g, 0.01 mol) in 40 ml. of anhydrous tetrahydrofuran, was heated at reflux for 4 hours and then stirred for 64 hours at 26° C. The reaction mixture was filtered and the filter cake was washed with ethyl acetate. The filtrate was concentrated in vacuo and the resulting residue was dissolved in methylene chloride. The methylene chloride solution was washed with 1% aqueous hydrochloric acid, dried overسodium sulfate and then concentrated in vacuo to yield a yellow oil which subsequently solidified. The solid residue was triturated with diethyl ether and the resulting solid was dissolved in carbon tetrachloride and recrystallized from diethyl ether and petroleum ether to yield 1-methyl-2-(4-bromophenyl)-2,3-dihydro-1H-2,1-benzazaphosphole-1-oxide (0.29 g, 100% yield) as white crystals having a melting point of 135°-136° C. and the following analysis:

Calculated: C, 52.51; H, 4.04; N, 4.35. Found: C, 52.10; H, 4.08; N, 4.32.

EXAMPLE 3

Under a static nitrogen atmosphere, a mixture of N-(3,4-dichlorophenyl)-P-[2-(chloromethyl)phenyl]-P-methylphosphinamide (1.4 g, 0.004 mol) and 1,5-diazabicyclo[5.4.0]undec-5-ene (0.65 g, 0.0041 mol) in 20 ml. of anhydrous tetrahydrofuran was heated at reflux for 4 hours and then stirred for 64 hours at 26° C. The reaction mixture was filtered and the filter cake was washed with ethyl acetate. The filtrate was concentrated in vacuo and the resulting residue was dissolved in 30 ml. of methylene chloride. The methylene chloride solution was washed with 1% aqueous hydrochloric acid, then water and subsequently dried over sodium sulfate and concentrated in vacuo to yield a gray glass. The glass residue was separated on a silica gel column using ethyl acetate as the eluant. Fractions containing the benzazaphosphole were combined and concentrated in vacuo to yield a solid residue. This solid residue was slurried in diethyl ether to yield 1-methyl-2-(3,4-dichlorophenyl)-2,3-dihydro-1H-2,1-benzazaphosphole-1-oxide (0.6 g, 48% yield) having a melting point of 152°-154° C. and the following analysis:

Calculated: C, 53.87; H, 3.88; N, 4.49; Cl, 22.72. Found: C, 53.78; H, 3.89; N, 4.51; Cl, 22.65.

EXAMPLE 4

Under a static nitrogen atmosphere, a mixture of N-(2,6-dimethylphenyl)-P-[2-(chloromethyl)phenyl]-P-methylphosphinamide (0.97 g, 0.00315 mol) and 1,5-diazabicyclo[5.4.0]undec-5-ene (0.50 g, 0.0033 mol) in 25 ml. of anhydrous tetrahydrofuran was heated at reflux for 16 hours. The reaction mixture was cooled and the organic phase was decanted from the solid precipitate. The organic phase was concentrated in vacuo and the residue was dissolved in methylene chloride. The methylene chloride solution was washed with 1% aqueous hydrochloric acid, dried, then concentrated in vacuo to yield a solid. The solid residue was triturated with diethyl ether and petroleum ether to yield 1-methyl-2-(2,6-dimethylphenyl)-2,3-dihydro-1H-2,1-benzazaphosphole-1-oxide (0.4 g, 47% yield) as a granular solid having a melting point of 128°-129° C.

EXAMPLE 5

Under a static nitrogen atmosphere, a mixture of N-(2-methoxyphenyl)-P-[2-(chloromethyl)phenyl]-P-methylphosphinamide (1.54 g, 0.005 mol) and 1,5-diazabicyclo[5.4.0]undec-5-ene (0.76 g, 0.005 mol) in 50 ml. of anhydrous tetrahydrofuran was heated at reflux for 16 hours. The organic layer was decanted from a white residue, concentrated in vacuo and the resulting residue was dissolved in methylene chloride. The methylene chloride solution was washed with 1% aqueous hydrochloric acid, then water, dried over magnesium sulfate and then concentrated in vacuo to yield a yellow oil. This oil was separated on a silica gel column using ethyl acetate as the eluant. Fractions containing the benzazaphosphole were combined and concentrated in vacuo to yield 1-methyl-2-(2-methoxyphenyl)-2,3-dihydro-1H-2,1-benzazaphosphole-1-oxide (1.02 g, 75% yield) as a yellow oil.

EXAMPLE 6

Under a static nitrogen atmosphere, a mixture of N-[3-(trifluoromethyl)phenyl]-P-[2-(chloromethyl)-phenyl]-P-methylphosphinamide (5.08 g, 0.015 mol) and 1,5-diazabicyclo[5.4.0]undec-5-ene (2.3 g, 0.015 mol) in 50 ml. of anhydrous tetrahydrofuran was heated at reflux for 4 hours and then stirred for 16 hours at 26° C. The reaction mixture was filtered and the filter cake was washed with ethyl acetate. The filtrate was concentrated in vacuo and the residue was dissolved in 50 ml. of methylene chloride. The methylene chloride solution was washed with 5% aqueous hydrochloric acid, then water, dried over sodium sulfate and concentrated in vacuo to yield an oil. This oil was separated on a silica gel column using ethyl acetate as the eluant. Fractions containing the benzazaphosphole were combined and concentrated in vacuo to yield a white solid. The solid was slurried in anhydrous diethyl ether to yield 1-methyl-2-(3-trifluoromethylphenyl)-2,3-dihydro-2,1-benzazaphosphole-1-oxide (2.3 g, 50% yield) having a melting point of 161°-163° C. and the following analysis:

Calculated: C, 57.88; H, 4.21; N, 4.50. Found: C, 57.77; H, 4.19; N, 4.47.

EXAMPLE 7

Under a static nitrogen atmosphere, a mixture of N-phenyl-P-[2-(chloromethyl)phenyl]-P-methylphosphinamide (78.5 g, 0.28 mol) and 1,5-diazabicyclo[5.4.0]undec-5-ene (47 g, 0.296 mol) in 280 ml. of anhydrous tetrahydrofuran was heated at reflux for 4 hours and then stirred for 16 hours a 26° C. The reaction mixture was filtered and the filter cake washed with ethyl acetate. The filtrate was concentrated in vacuo and the residue was dissolved in 500 ml. of methylene chloride. The methylene chloride solution was washed with 1% aqueous hydrochloric acid, 2.5% aqueous sodium bicarbonate, then water, dried over sodium sulfate and then concentrated in vacuo to yield a yellow glass-like residue. The glass-like residue was dissolved in 250 ml. of carbon tetrachloride, cooled during which period crystallization occurred and then filtered to yield a white precipitate. The precipitate was washed with carbon tetrachloride and recrystallized from methylcyclohexane to yield a solid residue. The solid was slurried in diethyl ether to yield 1-methyl-2-phenyl-2,3-dihydro-1H-2,1-benzazaphosphole-1-oxide (47.9 g, 70% yield) as a white powder having a melting point of 94°-97° C. and the following analysis:

Calculated: C, 69.13; H, 5.80; N, 5.76. Found: C, 68.95; H, 5.84; N, 5.72.

EXAMPLE 8

Under a static nitrogen atmosphere, a mixture of N-(4-phenoxyphenyl)-P-[2-(chloromethyl)phenyl]-P-methylphosphinamide (4.15 g, 0.011 mol) and 1,5-diazabicyclo[5.4.0]undec-5-ene (1.6 g, 0.01 mol) in 70 ml. of anhydrous tetrahydrofuran was heated at reflux for 16 hours. The reaction mixture was concentrated in vacuo and the residue was dissolved in methylene chloride. The methylene chloride solution was washed with 1% aqueous hydrochloric acid, dried over magnesium sulfate and then concentrated in vacuo to yield an oil. This oil was separated on a silica gel column using ethyl acetate as the eluant. Fractions containing the benzazaphosphole were combined and concentrated in vacuo to yield a white crystalline solid. Recrystallization of the solid from carbon tetrachloride yielded 1-methyl-2-(4-phenoxyphenyl)-2,3-dihydro-1H-2,1-benzazaphosphole-1-oxide (0.7g, 19% yield) as white crystals having a melting point of 176°-177° C.

EXAMPLE 9

The post-emergence herbicidal activity of the various compounds of this invention is demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/cm$^2$ absolute. The atomizer contains 6 ml. of a solution or suspension of the chemical and an amount of a cyclohexanone emulsifying agent mixture so that the spray solution or suspension contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
| --- | --- |
| 0-24% control | 0 |
| 25-49% control | 1 |
| 50-74% control | 2 |
| 75-99% control | 3 |
| 100% control | 4 |

The plant species utilized in these tests are identified by letter in accordance with the following legend:

| | |
| --- | --- |
| A-Canada Thistle* | G-Yellow Nutsedge* |
| B-Cocklebur | H-Quackgrass* |
| C-Velvetleaf | I-Johnsongrass* |
| D-Morningglory | J-Downy Brome |
| E-Lambsquarters | K-Barnyardgrass |

F-Smartweed

*Established from vegetative propagules.

TABLE I

| Compound of Example No. | WAT | kg/h | Plant Species | | | | | | | | | | |
|---|---|---|---|---|---|---|---|---|---|---|---|---|---|
| | | | A | B | C | D | E | F | G | H | I | J | K |
| 1 | 2 | 11.2 | 0 | 0 | 1 | 1 | 1 | 0 | 0 | 0 | 0 | 0 | 0 |
| 2 | 2 | 11.2 | 0 | 0 | 0 | 1 | 2 | 1 | 0 | 0 | 0 | 0 | 1 |
| 3 | 2 | 11.2 | 0 | 1 | 0 | 1 | 2 | 1 | 0 | 0 | 0 | 0 | 1 |
| 4 | 2 | 56.0 | 4 | 2 | 1 | 1 | 2 | 2 | 0 | 0 | 0 | 1 | 1 |
| 5 | 2 | 56.0 | 1 | 1 | 1 | 1 | 1 | 0 | 0 | 0 | 1 | 1 | 2 |
| 6 | 2 | 11.2 | 0 | 0 | 0 | 1 | 4 | 0 | 0 | 0 | 0 | 0 | 0 |
| 7 | 2 | 11.2 | 1 | 1 | 0 | 1 | 1 | 0 | 0 | 0 | 0 | 0 | 0 |
| 8 | 2 | 11.2 | 0 | 1 | 0 | 0 | 1 | 0 | 0 | 0 | 0 | 0 | 0 |

EXAMPLE 10

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table II.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75-100% control | 3 |

Plant species in the table are identified by the same code letters used in the previous example.

TABLE II

| Compound of Example No. | WAT | kg/h | Plant Species | | | | | | | | | | |
|---|---|---|---|---|---|---|---|---|---|---|---|---|---|
| | | | A | B | C | D | E | F | G | H | I | J | K |
| 1 | 2 | 11.2 | 0 | 0 | 0 | 0 | 0 | 0 | 0 | 0 | 0 | 0 | 0 |
| 2 | 2 | 11.2 | 0 | 0 | 0 | 0 | 0 | 0 | 0 | 0 | 0 | 0 | 0 |
| 3 | 2 | 11.2 | 0 | 0 | 0 | 0 | 3 | 0 | 0 | 0 | — | 0 | 1 |
| 4 | 2 | 56.0 | 1 | 0 | 3 | 0 | 0 | 0 | 0 | 0 | 0 | 0 | 1 |
| 5 | 2 | 56.0 | 0 | 0 | 0 | 0 | 0 | 3 | 0 | 0 | 0 | 0 | 3 |
| 6 | 2 | 11.2 | 0 | 0 | 0 | 0 | 1 | 0 | 0 | 0 | 0 | 0 | 1 |
| 7 | 2 | 11.2 | 0 | 0 | 0 | 0 | 0 | 0 | 0 | 0 | 0 | 0 | 0 |
| 8 | 2 | 11.2 | 0 | 0 | 0 | 0 | 0 | 0 | 0 | 0 | 0 | 0 | 1 |

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor or anti-foaming agent, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is depending upon the response desired in the plant as well as such other factors as the plant species and stage of development thereof, and the amount of rainfall as well as the specific benzazaphosphole employed. In foliar treatment for the control of vegetative growth, the active ingredients are applied in amounts from about 0.112 to about 56.0 or more kilograms per hectare. In pre-emergent treatments, the rate of application can be from about 0.56 to about 22.4 or more kilograms per hectare. In applications for the control of aquatic plants, the active ingredients are applied in amounts of from about 0.01 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

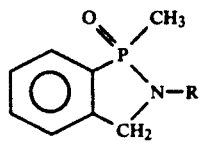

wherein R is selected from the group consisting of phenyl, phenoxyphenyl and substituted phenyl containing from one to three substituents individually selected from the class consisting of lower alkyl, lower alkoxy, halogen, and lower haloalkyl.

2. A compound according to claim 1 wherein R is substituted phenyl containing from one to three substituents individually selected from the class consisting of lower alkyl, lower alkoxy, halogen, and lower haloalkyl.

3. A compound according to claim 2 wherein the compound is 1-methyl-2-(2,6-dimethylphenyl)-2,3-dihydro-1H-2,1-benzazaphosphole-1-oxide.

4. A compound according to claim 1 wherein the compound is 1-methyl-2-(3,4-dichlorophenyl)-2,3-dihydro-1H-2,1-benzazaphosphole-1-oxide.

5. A compound according to claim 1 wherein the compound is 1-methyl-2-(2-methoxyphenyl)-2,3-dihydro-1H-2,1-benzazaphosphole-1-oxide.

6. A herbicidal composition comprising an inert adjuvant and a herbicidally effective amount of a compound of the formula

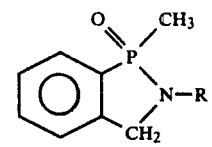

wherein R is selected from group consisting of phenyl, phenoxyphenyl and substituted phenyl containing from one to three substituents individually selected from the class consisting of lower alkyl, lower alkoxy, halogen, and lower haloalkyl.

7. A composition according to claim 6 wherein R is substituted phenyl containing from one to three substituents individually selected from the class consisting of lower alkyl, lower alkoxy, halogen, and lower haloalkyl.

8. A composition according to claim 7 wherein the compound is 1-methyl-2-(2,6-dimethylphenyl)-2,3-dihydro-1H-2,1-benzazaphosphole-1-oxide.

9. A composition according to claim 6 wherein the compound is 1-methyl-2-(2,3-dichlorophenyl)-2,3-dihydro-1H-2,1-benzazaphosphole-1-oxide.

10. A composition according to claim 6 wherein the compound is 1-methyl-2-(2-methoxyphenyl)-2,3-dihydro-1H-2,1-benzazaphosphole-1-oxide.

11. A method of controlling undesired plants which comprises contacting said plants or the plant growth medium with a herbicidal amount of a compound of the formula

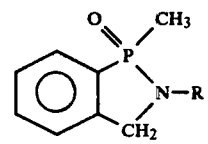

wherein R is selected from the group consisting of phenyl, phenoxyphenyl and substituted phenyl containing from one to three substituents individually selected from the class consisting of lower alkyl, lower alkoxy, halogen, and lower haloalkyl.

12. A method according to claim 11 wherein R is substituted phenyl with up to three substituents individually selected from the class consisting of lower alkyl, lower alkoxy, halogen, and lower haloalkyl.

13. A method according to claim 12 wherein the compound is 1-methyl-2-(2,6-dimethylphenyl)-2,3-dihydro-1-H-2,1-benzazaphosphole-1-oxide.

14. A method according to claim 11 where the compound is 1-methyl-2-(3,4-dichlorophenyl)-2,3-dihydro-1H-2,1-benzazaphosphole-1-oxide.

15. A method according to claim 11 wherein the compound is 1-methyl-2-(2-methoxyphenyl)-2,3-dihydro-1H-2,1-benzazaphosphole-1-oxide.

* * * * *